United States Patent [19]

Steiner et al.

[11] Patent Number: 5,453,546
[45] Date of Patent: Sep. 26, 1995

[54] METHOD FOR THE PRODUCTION OF β-IONONE FROM PSEUDOIONONE

[75] Inventors: Kurt Steiner, Starrkirch, Switzerland; Herwig Ertel, Grossostheim; Helmut Tiltscher, Munich, both of Germany

[73] Assignee: Hoffmann-La Roche Inc., Nutley, N.J.

[21] Appl. No.: 252,865

[22] Filed: Jun. 2, 1994

[30] Foreign Application Priority Data

Jun. 11, 1993 [CH] Switzerland .................. 1759/93

[51] Int. Cl.$^6$ .................................................. C07C 49/21
[52] U.S. Cl. ........................................................ 568/343
[58] Field of Search ............................................ 568/343

[56] References Cited

U.S. PATENT DOCUMENTS 4,565,894  1/1986  Hertel et al. ..................... 568/343

FOREIGN PATENT DOCUMENTS 2007509  1/1970  France ................................. 568/343
3431131  3/1986  Germany ............................. 568/343
547445   7/1977  U.S.S.R. ............................. 568/343

OTHER PUBLICATIONS

Carbonell, Cereal Foods World, vol. 36, #11, pp. 935–937 (1991).

*Primary Examiner*—James H. Reamer
*Attorney, Agent, or Firm*—George M. Gould; William H. Epstein; Bruce A. Pokras

[57] ABSTRACT

A process is described for the manufacture of β-ionone by the sulphuric acid-catalyzed cyclization of pseudoionone in a two-phase solvent system comprising concentrated sulphuric acid and a second solvent essentially immiscible with water, which process comprises using carbon dioxide liquefied under pressure as the second solvent. This process is carried out, inter alia, under a pressure of about 50 bar to about 150 bar and at temperatures from about −15° C. to about +15° C. prior to the subsequent stopping (quenching) of the cyclization reaction. The process in accordance with the invention is preferably carried out continuously and is an important intermediate stage in the synthesis of vitamin A.

8 Claims, 1 Drawing Sheet

METHOD FOR THE PRODUCTION OF β-IONONE FROM PSEUDOIONONE

BACKGROUND OF THE INVENTION

The present invention is concerned with a process for the manufacture of β-ionone from pseudoionone in a two-phase solvent system.

Many important industrial syntheses are carried out in heterogeneous liquid/liquid (two-phase) solvent systems, with the reaction taking place either directly at the phase boundary or in the bulk phase of the extractant.

Industrial examples of reactive heterogeneous liquid/liquid solvent systems are found, inter alia, in important intermediate stages in the synthesis of vitamin A. Here, reactants and products are distributed between two liquid phases.

Nowadays industrial syntheses are also systematically modified when they are in competition with existing and optimized production processes. In particular, the increased importance of product- and production-integrated environmental protection can mostly not be satisfied by new plant and equipment alone. Rather, changing the material system, if this is possible, frequently offers a much greater potential. The physiological concerns and the ecological problems connected with the chlorinated organic solvents used in the industrial process for the synthesis of vitamin A provide the motivation for development of an alternative process concept. In the industrial process, efforts are also made for economical and also ecological reasons to reduce the amount of sulphuric acid used, and thus reduce the environmentally problematic dilute acid obtained in the process, and such endeavours likewise provide a motivation.

The objective of the industrial synthesis of vitamin A is to build up the vitamin A structure with its 20 carbon atoms from readily available components, e.g., from petrochemicals. In β-ionone, a cyclic terpene ketone [4-(2,6,6-trimethyl-1-cyclohexen-1-yl)-3-buten- 2-one], there is already available a molecule which contains 13 carbon atoms including the terminal $C_6$ ring in the configuration corresponding to vitamin A. All large-scale processes for the synthesis of vitamin A therefore proceed via β-ionone as an intermediate.

The Isler synthesis (Roche) of 1948, the key step of which is based on the linking of a $C_{14}$ component formed from β-ionone with a $C_6$ component, can be regarded up to now as one of the most economically successful processes for the total synthesis of vitamin A. In its industrial implementation, this synthesis comprises 11 stages, of which the second consists of the cyclization of pseudoionone to β-ionone in the presence of sulphuric acid. β-ionone is converted via the glycidic ester synthesis into the $C_{14}$ component, 2-methyl-4-(2,6,6-trimethyl-1-cyclohexen-1-yl)- 2-buten-1-al (the "$C_{14}$ aldehyde"), which in turn is linked, via a Grignard reaction, with the $C_6$ component, 3-methyl-pent-2-en-4-yn-1-ol, synthesized in three reaction steps. Vitamin A acetate is obtained in crude form from the resulting oxenyne after partial Lindlar hydrogenation, acetylation with acetic anhydride, dehydration and rearrangement. After purification by crystallization and trans-esterification with methyl palmitate, vitamin A palmirate is formed, the commercial end product of the large-scale synthesis.

The central compound of all vitamin A syntheses is β-ionone, which can be obtained from pseudoionone (6,10-dimethylundeca- 3,5,9-trien-2-one) by a ring-closure reaction under the action of strong protonic acids. In this ring-closure reaction, there also simultaneously results α-ionone [4-(2,6,6-trimethyl-2-cyclohexen- 1-yl)-3-buten-2-one] which differs from the isomeric β-ionone only by the position of the double bond in the ring with the formation of an asymmetric carbon atom having the (R) configuration. α-ionone is principally used in the perfume industry as an odorant precursor.

The use of chlorinated hydrocarbons as solvents in organic syntheses is widespread. The exceptional solvent power of methylene chloride, not only for terpenoid compounds but also for a majority of the polymeric byproducts formed in the synthesis, is the basis for its use in industrial vitamin A production. In addition, the high density of methylene chloride favours dispersion of the sulphuric acid during the cyclization of pseudoionone, which permits a high mass transfer rate in the two-phase system. At the same time, however, the subsequent separation of the sulphuric acid phase is made more difficult. As already indicated above, the use of chlorinated solvents such as, for example, methylene chloride, is more and more the subject of ecological debate. Despite reprocessing of the solvent, leakage losses in industrial plants are unavoidable in view of the high vapour pressure of methylene chloride. Chlorinated hydrocarbons which are released are suspected of being capable of causing changes in the constitution of the atmosphere. In addition, these solvents are considered to have a carcinogenic action, so that their use in the production of pharmaceutical products and foodstuffs is questionable, not least from a psychological point of view. Despite the advantages which chlorinated hydrocarbons offer in industrial production, for these reasons there is an intensive search for replacement by alternative solvents and processes.

In the industrial-scale plant, pseudoionone is continuously reacted completely with highly concentrated, e.g., 98%, sulphuric acid, with β-ionone being obtained in a yield of about 90%. The pseudoionone is taken from intermediate storage tanks via metering pumps and is dissolved in methylene chloride. The thus-diluted educt, pseudoionone, is mixed intensively in the reaction zone with sulphuric acid in a weight ratio of about 1:2 (educt:acid). The acid is soluble in methylene chloride to only a small extent, so that a two-phase liquid/liquid system forms in which the reaction is initiated at the phase boundary. The pseudoionone educt reacts at the surface of the dispersed sulphuric acid droplets. The products formed remain bound in the acid phase. The heat liberated in the strongly exothermic reaction is removed by pre-cooling the pseudoionone/methylene chloride stream and intensively cooling in the reactor to maintain a temperature of 0° to 5° C., especially about 0° C. Since β-ionone in contact with sulphuric acid forms high molecular weight, polymeric byproducts with increasing reaction time, it is necessary to suppress further reaction. In a so-called quenching stage, the sulphuric acid is diluted by the metered addition of water to a sufficient extent, normally to an about 18% aqueous solution, so that with simultaneous separation of the resulting organic and the acidic aqueous phase the reaction is stopped. The liberated enthalpy of dilution must be removed in this case. Since it is also extremely desirable, for economical and ecological reasons, to feed the sulphuric acid back into the reaction system for re-use, the strongly diluted aqueous sulphuric acid solution must be purified and concentrated, which because of the required degree of concentration (from about 18% up to about 98%) is very energy-intensive and costly.

SUMMARY OF THE INVENTION

It will be clear from the above remarks that there is an urgent need to replace the methylene chloride solvent hitherto used in the production process for preparing β-ionone by a more suitable solvent which does not have the aforementioned disadvantages of methylene chloride. It has now surprisingly been found that the use of liquefied carbon dioxide (maintained under pressure) meets this need.

The process in accordance with the invention for the manufacture of β-ionone under low temperature and high pressure by the sulphuric acid-catalyzed cyclization of pseudoionone in a two-phase solvent system of concentrated sulphuric acid and a second solvent essentially immiscible with water comprises using carbon dioxide liquefied under high pressure as the second solvent.

DETAILED DESCRIPTION OF THE INVENTION

Figure 1:
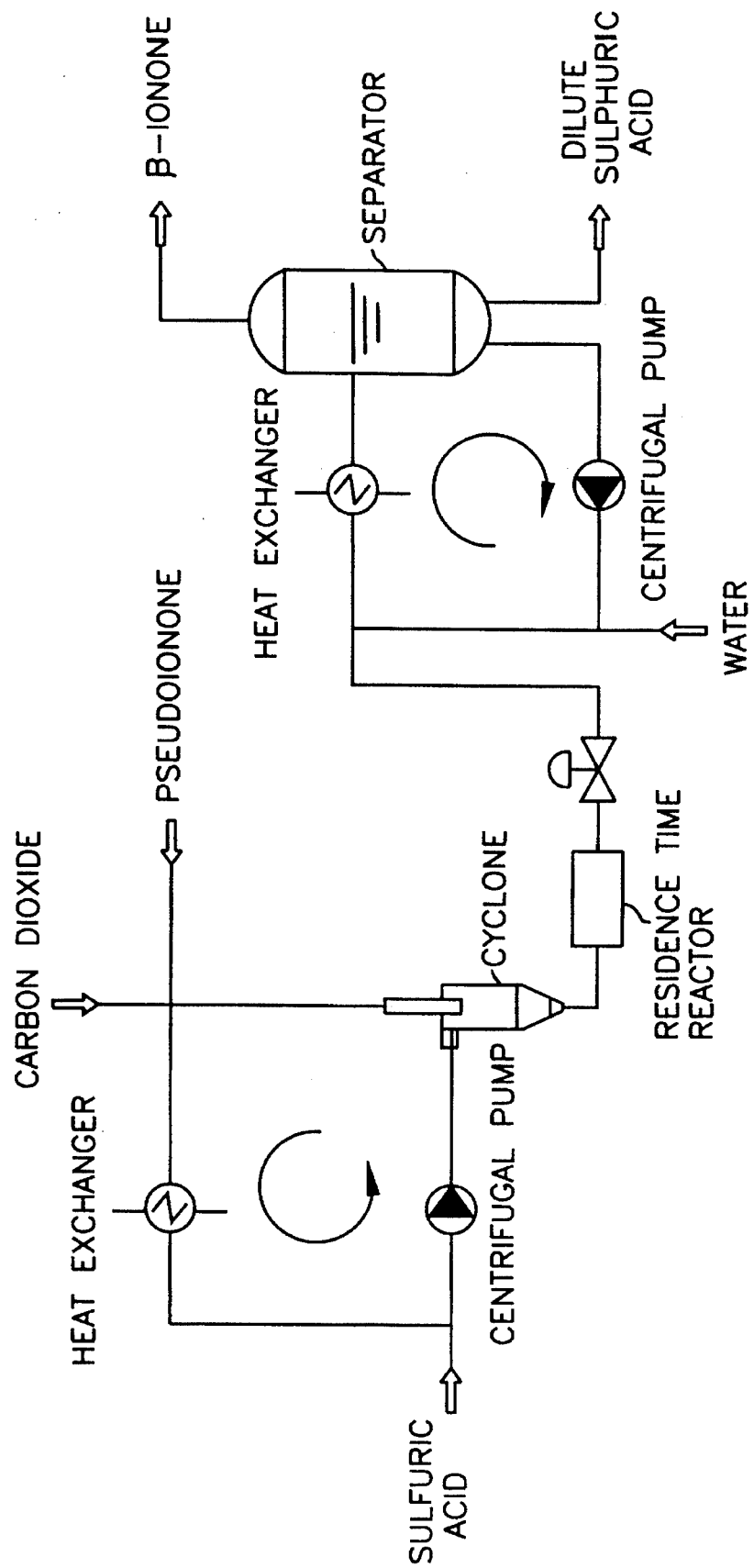
FIG. 1: Schematic diagram of the apparatus for carrying out a continuous trial of the process in accordance with the invention for making β-ionone from pseudoionone.

The process of the invention comprises the manufacture of β-ionone from pseudoionone under low temperature and high pressure by the sulphuric acid-catalyzed cyclization of pseudoionone in a mixture formed by mixing a two-phase solvent system, wherein concentrated sulphuric acid comprises the first phase and pseudoionone dissolved in liquid carbon dioxide comprises the second phase. Any conventional conditions known in the art useful for the reaction of pseudoionone to β-ionone by the sulphuric acid-catalyzed cyclization of pseudoionone in a two-phase solvent system, wherein an organic solvent which is essentially insoluble in water is used as the solvent for the pseudoionone, may be used, with the exception that the reaction of the invention must occur under pressure to maintain the carbon dioxide in its liquid form.

Preferably, the process of the invention for the manufacture of β-ionone from pseudoionone comprises:

1) providing a two-phase solvent system under high pressure wherein the first phase comprises an aqueous solution of at least 85 weight percent sulfuric acid, and the second phase comprises liquid carbon dioxide having pseudoionone dissolved therein;

2) mixing the two phases at a temperature from about −15° C. to about 15° C. to obtain a mixture of the two phases;

so that the pseudoionone is converted to β-ionone.

Thus, the present invention also comprises an improvement on the conventional process for the manufacture of β-ionone by the sulphuric acid-catalyzed cyclization of pseudoionone at low temperature in a two-phase solvent system which is mixed to obtain a mixture of the two phases, wherein one phase comprises concentrated sulphuric acid and the other phase comprises an organic solvent essentially immiscible with water with pseudoionone dissolved therein, wherein the improvement comprises the use of liquid carbon dioxide under high pressure in place of the organic solvent.

The initial reaction step of the process in accordance with the invention is the protonation of the pseudoionone educt, which is mainly dissolved in the carbon dioxide phase, by the sulphuric acid which functions as a so-called reaction promoter. The protonation is followed within a very short time by the actual transformation of the educt into the desired β-ionone product, namely by cyclization of the protonated pseudoionone. Pertinent experiments have shown that the protonation and the subsequent cyclization occur at the phase boundaries between the liquefied carbon dioxide and the sulphuric acid phase. The (still) unreacted pseudoionone then remains in the carbon dioxide phase while the product, which is in protonated form, is taken up in the sulphuric acid phase. Only on the addition of cooled water, aqueous alkali, in particular aqueous ammonium hydroxide solution having a concentration of from 2 to 4 mol/l (about 7 to 14%), or strongly diluted sulphuric acid, especially about 30 to 40%, sulphuric acid, preferably at 0° to 10° C., to the reaction mixture can the deprotonation of this product occur. The reaction is thereby terminated.

The experimental results from the reaction of pseudoionone with concentrated sulphuric acid reveal a more complex reaction pattern. However, this reaction pattern is not unique to the present invention, but is also inherent in the conventional process wherein the pseudoionone is dissolved in an organic solvent which is essentially immiscible with water. Thus, the process of the present invention may be optimized by routine experimentation familiar to those skilled in the art. In the reaction, pseudoionone reacts with sulphuric acid in parallel ways to give α- and β-ionone, with the ratio of these two products depending on the reaction conditions used in each case, such as, for example, the concentration of sulphuric acid, reaction temperature (range), weight ratio of educt and sulphuric acid and reaction time. In addition, the direct rearrangement of α-ionone to β-ionone is possible under the action of sulphuric acid. Furthermore, both the pseudoionone educt and the desired β-ionone product as well as the α-ionone, regarded as a byproduct of the process in accordance with the invention, tend to undesired polymer formation, especially under the influence of highly concentrated sulphuric acid. Both the contact of protonated compounds with unprotonated educt (pseudoionone) from the carbon dioxide phase and also the attack of excess sulphuric acid on products already formed are possible. The polymer compounds of differing chemical composition arise in significant amounts after even the shortest reaction times such as, for example, 2.5 minutes, and their proportion of the total product increases continuously during the reaction and is, inter alia, also dependent on the acid concentration and on the temperature at which the two phases are mixed.

These observations lead to the conclusion that not only the influencing parameters of the chemical reaction system, but also the reaction procedure have to be adjusted to afford an optimum yield of the desired β-ionone product. While the sulphuric acid participating in the reaction determines the ratio of the simultaneously formed α- and β-ionone products, it is an object of the reaction procedure to stop the reaction before passing the maximum proportion of β-ionone. The residence time of the reacted components in the reaction space thus attains decisive significance and can be chosen through the use of routine experiments in such a way that, inter alia, the formation of polymeric byproducts is suppressed.

Since in the process in accordance with the invention the carbon dioxide should be present in the liquid state, it has to be under high pressure, i.e., pressure sufficient to maintain the carbon dioxide in the liquid state at the temperature under which the reaction is carried out. The pressure under which the process is carried out generally lies in the range of about 50 bar to about 150 bar, preferably in the range of about 80 bar to about 120 bar.

As far as the concentration of the sulphuric acid is concerned, it has been observed that, in general, a relatively high concentration leads to the desired pronounced formation of β-ionone, while the use of relatively dilute (less than about 60 percent) sulphuric acid initiates (practically) no cyclization of the pseudoionone. If about 75 to 85 percent sulphuric acid is used, the undesired α-ionone is principally formed. Thus, the concentration of the sulphuric acid used in the process of the invention is at least 85 percent. Sulphuric acid in a concentration between about 95 and about 98 percent is preferably used.

The molar or mass (weight) ratio of sulphuric acid to pseudoionone in the mixture of the two phases is a further reaction parameter. It has been determined that pseudoionone in the two-phase system of liquefied carbon dioxide (as solvent for the educt)/sulphuric acid reacts completely only at a sulphuric acid:pseudoionone molar ratio greater than 2:1 (mass ratio 1:1) at a reaction temperature of about 5° C. Expressed in another way, at least twice the molar amount of sulphuric acid is required at this temperature to achieve complete protonation of the basic centers of the pseudoionone. Too much acid (and/or acid which is too concentrated) leads to excessive formation of polymeric byproducts, which is also the case if there is too little sulphuric acid. A maximum yield of β-ionone is achieved, for example, at about 5° C. if the molar ratio of sulphuric acid:pseudoionone in the reaction mixture of the invention is about 3:1 (mass ratio 1.5:1). Of course, the reaction temperature here exerts an influence on the yield at a particular molar ratio, in that higher reaction temperatures, e.g., temperatures above 15° C., lead to smaller yields because of increased polymer formation. The process in accordance with the invention is suitably carried out at a molar ratio of sulphuric acid:pseudoionone in the range of about 2:1 to about 5:1, preferably of about 2.5:1 to about 3.5:1.

The mass ratio of carbon dioxide to pseudoionone in the liquid carbon dioxide phase is preferably from 100:1 to 100:5.

In the determination of the reaction temperature, it has to be taken into account, inter alia, that temperatures which are too high lead to excessive polymer formation, while temperatures which are too low lead to an unsatisfactorily slow reaction. In general, the process in accordance with the invention is carried out at low temperatures, i.e., from about −15° C. to about 15° C. The temperature range from about −5° C. to about 10° C., especially that from about 0° C. to about 5° C., is preferably used, with the narrower range permitting particularly good yields of β-ionone with a satisfactory reaction rate and without excessive formation of undesired polymer byproducts.

Taking into account the other reaction conditions and the desire for the highest possible yield of β-ionone with minimum production of undesired byproducts, such as α-ionone and polymeric compounds, the conversion realized in accordance with the invention of pseudoionone into β-ionone in the reaction stage (prior to the quench stage) takes place in about 10 minutes to about 40 minutes.

During the reaction carried out in accordance with the invention, intensive mixing of the sulphuric acid and the carbon dioxide phases is advantageous, since the protonation and subsequent cyclization of pseudoionone takes place under the influence of sulphuric acid at the phase boundary. In this way, i.e., by generation of as large as possible a mass-transfer area with small droplet radii, the best possible utilization of the amount of acid used can be achieved and the reaction can be efficiently carried out.

The aforementioned quenching, performed after the reaction stage, which permits a rapid dilution of the reaction mixture, resulting deprotonation of the product, separation of the reaction mixture into an aqueous acid phase and an organic phase (the product phase) and also the suppression of the undesired polymerization, is advantageously carried out by the addition of cooled water, aqueous alkali or strongly diluted sulphuric acid, preferably at about 0° to 10° C. The quenching permits a rapid and complete termination of the chemical reaction with rapid removal of the amount of heat generated. The amount of liquid, preferably water, used for the quenching is advantageously that required to achieve a dilution of the sulphuric acid phase to about 40 to 50 percent. The separated product phase is worked up in order to isolate the pure β-ionone, preferably by introducing the product phase into a high-pressure extraction column and extracting with carbon dioxide as solvent. After removing the solvent, which can be recycled, the desired β-ionone is obtained. The dilute sulphuric acid phase is freed from organic residues by conventional means, e.g., filtration or continuous centrifugation, and is subsequently concentrated, likewise in a manner known per se, so that the resulting highly concentrated sulphuric acid can be recycled.

The process in accordance with the invention can be carried out either batchwise or continuously. However, preference is given to continuous operation in which, inter alia, as much as possible of the liquefied carbon dioxide, any unreacted pseudoionone and also the sulphuric acid which has been concentrated, are reintroduced into the reaction system.

In a typical, continuously operated industrial plant, which permits the use of liquefied carbon dioxide under pressure as the solvent for the educt, liquefied carbon dioxide is circulated in the reaction zone by means of a dispersing device. Pseudoionone is metered into the circulating stream and homogeneously dissolved in the continuous phase in a static mixer. The sulphuric acid is, in turn, dispersed in the educt phase by a dispersing device, conveniently by injection directly upstream of the dispersing device. Almost immediately, a large mass-transfer area is achieved by intensive mixing of the two-phase system. This produces a state of mixing which lies between the limiting cases of completely mixed bulk phases and of fixed unmixed acid droplets. Best possible utilization of the amount of acid used can be achieved by generating a large mass-transfer area with small droplet radii. However, due to the protonated organic compounds bound to the droplet surfaces where there is an excess of educt, polymerization is favoured by an ionic mechanism. Besides the optimization of the pseudoionone concentration in the continuous carbon dioxide phase, rapid removal of the acid product phase, for example by introducing the heavy product phase into a hydrocyclone, can suppress this polymerization. This permits a rapid separation of the organic protonated compounds from unconsumed pseudoionone and suppresses the formation of high molecular weight byproducts. Since the yield of β-ionone passes through a maximum with time, care must be taken to ensure a narrow residence time distribution in the reaction zone. The heat generated in the exothermic reaction must be removed and the reaction must be completely stopped. By cooling the circulating stream in the static mixer, it is possible to control the heat evolved in the reaction. While unconsumed pseudoionone in the carbon dioxide solvent is recirculated, e.g., into a hydrocyclone, the acid product phase is drawn off. In order to complete the cyclization reaction, the acid product phase can pass through a residence time reactor. The way in which the material flows are directed in the reaction zone (recirculation of the unreacted, dissolved educt and linear passage of the acid/product phase) makes it possible to realize the desired narrow residence time distribution of the products formed in the reaction region of the plant.

In order to completely stop the chemical reaction with rapid removal of the heat, a quenching zone is arranged downstream of the reaction zone. The complex reaction mixture, comprising protonated organic substances and concentrated sulphuric acid, must be quenched here, which is achieved by rapid dilution of the acid. The quenching zone can also be arranged as a circuit, permitting intensive mixing and cooling to remove the heat of dilution. The dilution of the acid product phase, preferably to a sulphuric acid content of about 45%, leads to separation into an organic product phase and aqueous sulphuric acid phase. The organic products pass on to the purification stage. Organic residues can be removed from at least a part of the sulphuric acid phase, which can subsequently be concentrated.

The quenching can also be carried out by the addition of a cooled aqueous alkali, especially aqueous ammonia, the complex reaction mixture likewise being separated with the formation of inorganic salt solutions. The metered addition of aqueous ammonia, conveniently in a molar concentration of 2 to 4 (per 1; about 7 to 14%) at 0 to 10° C., results in the organic compounds separating out as a light phase and the ammonium sulphate formed remaining in solution in the aqueous phase. Salt encrustations are thus avoided. After treating the aqueous phase with an organic solvent, e.g., acetone, and evaporating the ammonium sulphate remains as a white powder. After filtration water and organic impurities are removed with the solvent. The organic reaction products previously withdrawn are stripped with liquid carbon dioxide, by which means the ionones can be separated from the high molecular weight polymer products.

As a further variant, quenching can also be carried out with cooled, strongly diluted sulphuric acid, advantageously at 0° to 10° C. and a concentration of 30 to 40 weight percent, After carrying out the process in accordance with the invention and subsequently isolating the desired β-ionone, decompression allows the removal of carbon dioxide, which is not recirculated to the system, from the synthesis products without residues. In addition, as a physiologically inert substance, this solvent also requires no special precautions in the production process itself, so that complicated protective measures for the personnel concerned in the interests of good manufacturing practice can be omitted. The use of carbon dioxide as solvent additionally offers an opportunity for environmentally-friendly, and thus ecologically sensible, utilization of this substance produced in excess in incineration processes, especially since, as a greenhouse gas, it is increasingly the centre of attention in environmental politics. A further advantage of the process in accordance with the invention compared with the existing use of chlorinated hydrocarbons as solvents lies in the reduction of the amount of the reaction promoter sulphuric acid, the reprocessing or disposal of which takes up a considerable part of the production costs. In comparison with methylene chloride, carbon dioxide has a low solvent power for sulphuric acid, resulting in the removal of less of the acid from the reaction system by the solvent.

The process in accordance with the invention is illustrated by the following Example.

EXAMPLE

The apparatus used for carrying out a continuous trial of the process in accordance with the invention is shown in FIG. 1:

Liquid carbon dioxide ($CO_2$) under pressure is used as solvent for the pseudoionone. The pseudoionone educt is continuously metered into and dissolved in the circulating $CO_2$ stream. In addition, the small amount of $CO_2$ dissolved in the heavy (sulphuric acid) phase, which thus leaves the gas circuit, must be replaced.

The gas stream thus loaded with pseudoionone is precooled. Just upstream of the centrifugal pump, concentrated sulphuric acid is metered in. The centrifugal pump serves on the one hand as a conveying device and on the other hand as a dispersing device. The emulsion thus formed passes into a separator (hydrocyclone) and is separated into the light gas phase and the heavy sulphuric acid-containing phase. The light phase is recirculated and the heavy phase is passed into a residence time reactor having a variable volume. After leaving the residence time reactor, the acid product phase is depressurized to ambient pressure and is quenched by feeding in dilute sulphuric acid. After removal of the heat of dilution, the dilute sulphuric acid is separated from the β-ionone product in a separator.

In the trials carried out, the throughput in the reaction stream lies in the range of 40 to 60 kg/h. Between 1 and 5 weight percent (wt. %), but generally 2 wt. %, of pseudoionone are dissolved in the circulating stream. This loading is restricted not by the solubility of the pseudoionone in carbon dioxide, but by the heating (because of the protonation energy to be removed) of the reaction stream which is limited to 60 kg/h. Thus, with a loading of 2 wt. % and a throughput in the reaction stream of 50 kg/h, the temperature increase is already about 9° C., i.e., the circulating stream has to be cooled upstream of the dispersing device by this temperature below the desired reaction temperature.

In order to limit effectively the formation of α-ionone, it has been found that the concentration of the sulphuric acid should be at least 90 percent. The continuous trials are carried out with 95 to 98 percent sulphuric acid, the yields with 98 percent sulphuric acid being slightly better.

When quenching with dilute sulphuric acid to an acid concentration of 55 percent, decomposition of the β-ionone (after 15 minutes, at 20° C.) was found to be about 4 wt. %. At acid concentrations below 45 percent there is hardly any noticeable decomposition. For this reason, quenching in the continuous trials was generally carried out by feeding in 35 percent sulphuric acid to give a sulphuric acid concentration of 40%. The throughput of the recirculated sulphuric acid stream is about 16 kg/h.

The results of the trials are shown in the following Table:

| Trial | No.1 | No.2 | No.3 | No.4 | No.5 | No.6 | No.7 | No.8 | No.9 | No.10 | No.11 | No.12 |
|---|---|---|---|---|---|---|---|---|---|---|---|---|
| Conc. $H_2SO_4$(%) | 95–98 | 95–98 | 95–98 | 95–98 | 95–98 | 95–98 | 95–98 | 95–98 | 95–98 | 95–98 | 95–98 | 95–98 |
| $H_2SO_4$/pseudo-ionone[kg/kg] | 1:1 | 1:1 | 1:1 | 1:1 | 1:1 | 1:1 | 1.57:1 | 1.57:1 | 1.57:1 | 2.47:1 | 2.47:1 | 2.47:1 |
| Pseudoionone/$CO_2$(wt. %) | 2–4 | 2–4 | 2–4 | 2–4 | 2–4 | 2–4 | 2–4 | 2–4 | 2–4 | 2–4 | 2–4 | 2–4 |
| Pressure (bar) | 80–100 | 80–100 | 80–100 | 80–100 | 80–100 | 80–100 | 80–100 | 80–100 | 80–100 | 80–100 | 80–100 | 80–100 |
| Reaction temperature (°C.) | 5 | 5 | –10 | –10 | 25 | 25 | 5 | 5 | 5 | 5 | 5 | 5 |
| Reaction time (min.) | 10 | 20 | 10 | 30 | 10 | 20 | 10 | 20 | 30 | 20 | 30 | 40 |
| Yield (wt. %;±5) | 60 | 70 | 40 | 50 | 52 | 45 | 70 | 80 | 90 | 70 | 75 | 70 |

We claim:

1. A process for the manufacture of β-ionone from pseudoionone comprising:

1) providing a two-phase solvent system under high pressure wherein the first phase comprises an aqueous solution of at least 85 weight percent sulfuric acid, and the second phase comprises liquid carbon dioxide having pseudoionone dissolved therein;

2) mixing the two phases at a temperature from about −15° C. to about 15° C. to obtain a mixture of the two phases;

so that the pseudoionone is converted to β-ionone.

2. The process of claim 1 wherein said mixture contains no organic solvent.

3. The process of claim 2, wherein the pressure is in the range from about 80 bar to about 120 bar.

4. The process of claim 3 wherein the concentration of the sulfuric acid is from about 95 percent to about 98 percent.

5. The process of claim 3, wherein the molar ratio of sulphuric acid:pseudoionone in the mixture is from about 2:1 to about 5:1.

6. The process of claim 5, wherein the molar ratio of sulphuric acid:pseudoionone in the mixture is from about 2.5:1 to about 3.5:1

7. The process of claim 6 wherein the temperature of the mixture is from about −5° C. to about 10° C.

8. The process of claim 7 wherein the temperature of the mixture is from about 0° C. to about 5° C.

* * * * *